(12) United States Patent
Mottola et al.

(10) Patent No.: US 11,717,318 B2
(45) Date of Patent: Aug. 8, 2023

(54) NESTED NEEDLES FOR SPINAL CYST TREATMENT

(71) Applicant: Merit Medical Systems, Inc., South Jordan, UT (US)

(72) Inventors: Jim Mottola, West Jordan, UT (US); Michael Hallisey, Wethersfield, CT (US)

(73) Assignee: Merit Medical Systems, Inc., South Jordan, UT (US)

( * ) Notice: Subject to any disclaimer, the term of this patent is extended or adjusted under 35 U.S.C. 154(b) by 118 days.

(21) Appl. No.: 16/007,153

(22) Filed: Jun. 13, 2018

(65) Prior Publication Data

US 2018/0353207 A1 Dec. 13, 2018

Related U.S. Application Data

(60) Provisional application No. 62/603,805, filed on Jun. 13, 2017.

(51) Int. Cl.
*A61B 17/34* (2006.01)

(52) U.S. Cl.
CPC .. *A61B 17/3421* (2013.01); *A61B 2017/3454* (2013.01); *A61B 2017/3456* (2013.01)

(58) Field of Classification Search
CPC ............ A61B 17/3423; A61B 17/3472; A61B 2017/3454; A61B 2017/3456; A61B 17/34; A61B 17/3401; A61B 17/3403; A61B 17/3415; A61B 17/3417; A61B 17/3421; A61B 17/3478; A61B 17/3474; A61B 17/1642; A61B 17/1671; A61B 17/1757; A61B 10/02; A61B 10/0233; A61B 2010/045
See application file for complete search history.

(56) References Cited

U.S. PATENT DOCUMENTS

| | | | |
|---|---|---|---|
| 3,993,079 A | | 11/1976 | Henriques de Gatztanondo |
| 4,931,042 A | * | 6/1990 | Holmes .............. A61B 17/3496 604/164.12 |
| 5,169,387 A | | 12/1992 | Kronner |
| 5,250,036 A | * | 10/1993 | Farivar ............. A61M 25/0631 604/164.01 |
| 2003/0083592 A1 | * | 5/2003 | Faciszewski ...... A61B 10/0266 600/564 |

(Continued)

FOREIGN PATENT DOCUMENTS

WO 2015073397 5/2015

OTHER PUBLICATIONS

International Search Report and Written Opinion dated Oct. 5, 2018 for PCT/US2018/037232.
European Search Report dated Feb. 4, 2021 for EP18818124.2.

*Primary Examiner* — Ashley L Fishback
(74) *Attorney, Agent, or Firm* — Dorsey & Whitney LLP

(57) ABSTRACT

Devices and methods used to drain a spinal cyst are disclosed. An opening may be created by a medical device, such as a nested needle assembly, that is inserted percutaneously into a facet joint adjacent to the cyst. The needle assembly may include a first elongate member, needle or introducer cannula; a second elongate member, inner cannula, needle, or trocar; and a piercing needle. The piercing needle may be used to microfenestrate a wall of the cyst such that fluid within the cyst is permitted to drain from the cyst.

15 Claims, 10 Drawing Sheets

(56) References Cited

U.S. PATENT DOCUMENTS

| | | |
|---|---|---|
| 2010/0241160 A1 | 9/2010 | Murphy |
| 2012/0316500 A1* | 12/2012 | Bierman ........... A61M 25/0662 |
| | | 604/164.1 |
| 2013/0090654 A1 | 4/2013 | Clancy |
| 2015/0297246 A1* | 10/2015 | Patel .................. A61B 17/3478 |
| | | 606/79 |
| 2016/0030017 A1 | 2/2016 | McWeeney et al. |
| 2016/0089180 A1 | 3/2016 | Entabi |
| 2016/0151089 A1 | 6/2016 | Cavilla et al. |

* cited by examiner

NESTED NEEDLES FOR SPINAL CYST TREATMENT

RELATED APPLICATIONS

This application claims priority to U.S. Provisional Application No. 62/603,805 filed on Jun. 13, 2017 and titled "Percutaneous Coaxial Needle For Imaged Guided Synovial, Spinal and Tarlov Cyst Access And Microfenestration," which is hereby incorporated by reference in its entirety.

TECHNICAL FIELD

The present disclosure relates generally to elongate medical devices such as needles, including needle assemblies. More specifically, in some embodiments, the present disclosure relates to nested needle assemblies used, for example, to access and microfenestrate a spinal synovial or Tarlov cyst in order to drain the cyst.

BRIEF DESCRIPTION OF THE DRAWINGS

The embodiments disclosed herein will become more fully apparent from the following description and appended claims, taken in conjunction with the accompanying drawings. These drawings depict only typical embodiments, which will be described with additional specificity and detail through use of the accompanying drawings in which:

DETAILED DESCRIPTION

Figure 1:
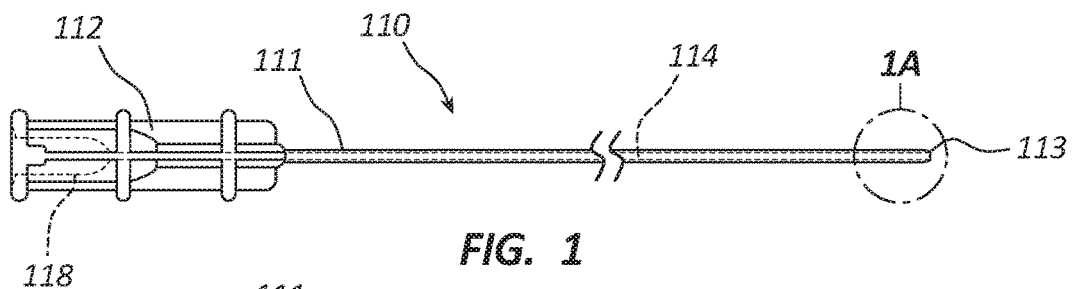
FIG. 1 is a side view of an introducer cannula of a cyst needle assembly.

Radiculopathy associated with a patient's back may be caused by a spinal synovial or Tarlov cyst. The cyst may apply pressure to the spinal column or nerve root resulting in pain, numbness, or weakness in the buttocks and lower extremities. In certain instances, the cyst may be drained through a microfenestration. The microfenestration may be created by a medical device, such as a nested needle assembly, that is inserted percutaneously into a facet joint adjacent to the cyst. Imaging, such as computer tomography may be used for guidance. In certain embodiments, the needle assembly may comprise a first elongate member, such as a needle or introducer cannula; a second elongate member, such as an inner cannula, needle, or trocar; and a piercing needle. The piercing needle may be used to microfenestrate a wall of the cyst such that fluid within the cyst is permitted to drain from the cyst.

Embodiments may be understood by reference to the drawings, wherein like parts are designated by like numerals throughout. It will be readily understood by one of ordinary skill in the art having the benefit of this disclosure that the components of the embodiments, as generally described and illustrated in the figures herein, could be arranged and designed in a wide variety of different configurations. Thus, the following more detailed description of various embodiments, as represented in the figures, is not intended to limit the scope of the disclosure, but is merely representative of various embodiments. While the various aspects of the embodiments are presented in drawings, the drawings are not necessarily drawn to scale unless specifically indicated.

Various features are sometimes grouped together in a single embodiment, figure, or description thereof for the purpose of streamlining the disclosure. Many of these features may be used alone and/or in combination with one another.

The phrases "coupled to" and "in communication with" refer to any form of interaction between two or more entities, including mechanical, electrical, magnetic, electromagnetic, fluid, and thermal interaction. Two components may be coupled to or in communication with each other even though they are not in direct contact with each other. For example, two components may be coupled to or in communication with each other through an intermediate component.

The directional terms "distal" and "proximal" are given their ordinary meaning in the art. That is, the distal end of a medical device means the end of the device furthest from the practitioner during use. The proximal end refers to the opposite end, or the end nearest the practitioner during use. As specifically applied to the needle portion of a needle assembly, the proximal end of the needle refers to the end nearest the hub and the distal end refers to the opposite end, the end nearest the sharpened end of the needle. Further, if at one or more points in a procedure a physician changes the orientation of a needle, as used herein, the term "proximal"

end" always refers to the hub end of the needle (even if the distal end is temporarily closer to the physician).

"Fluid" is used in its broadest sense, to refer to any fluid, including both liquids and gases as well as solutions, compounds, suspensions, etc., which generally behave as fluids.

FIGS. 1-10C illustrate several views of needle assembly devices and related components. In certain views each device may be coupled to, or shown with, additional components not included in every view. Further, in some views only selected components are illustrated, to provide detail into the relationship of the components. Some components may be shown in multiple views, but not discussed in connection with every view. Disclosure provided in connection with any figure is relevant and applicable to disclosure provided in connection with any other figure or embodiment.

FIGS. 1-6B depict an embodiment of a cyst needle assembly 100. In the illustrated embodiment, the cyst needle assembly 100 is comprised of a first elongate member, introducer cannula 110; a second elongate member, trocar 120, and a piercing needle 130.

Figure 1A:
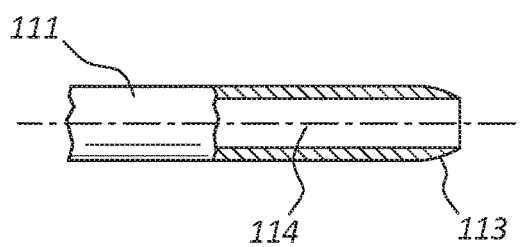
FIG. 1A is a side view of a distal portion of the introducer cannula of FIG. 1.

As illustrated in FIGS. 1-1A, the introducer cannula 110 comprises a tubular shaft 111 and a cannula hub 112. The tubular shaft 111 has a lumen 114 and a distal end 113. The distal end 113 is configured to be blunt and to resist penetrating tissue. In other words, the distal end 113 can be pushed against tissue, such as skin, and will not puncture or cut the tissue. As illustrated in FIG. 1A, the distal end 113 is squared off relative to a longitudinal axis of the tubular shaft 111 and a wall of the tubular shaft 111 is radiused to form the blunt distal end 113. In other embodiments, the blunt distal end 113 may be shaped in any suitable shape configured to resist penetrating tissue, such as a non-radiused end, an outwardly radiused end, etc. In some embodiments, the distal end 113 may be sharpened and configured to penetrate tissue. The tubular shaft 111 may be formed from nitinol. In other embodiments, the tubular shaft 111 may be formed from any suitable medical-grade metal, such as stainless steel, titanium, etc. The outer diameter of the tubular shaft 111 may range from 18 gauge to 25 gauge, including from 20 gauge to 22 gauge. The length of the tubular shaft 111 may range from about 2.5 cm to about 20 cm, including from about 8 cm to about 14 cm, or from about 4.5 cm to about 6 cm.

With continued reference to FIG. 1, the cannula hub 112 is coupled to and disposed at a proximal end of the tubular shaft 111. The cannula hub 112 may be configured to be gripped by fingers of a clinician. In some embodiments, the cannula hub 112 may be generally cylindrical in shape and comprise ribs or other features to enhance gripability. In the illustrated embodiment, the cannula hub 112 comprises an internal cavity 118 that is in fluid communication with the lumen 114 of the tubular shaft 111. The internal cavity 118 may be configured to receive a portion of the trocar 120 (not shown) as will be described below. The cannula hub 112 may be coupled to the tubular shaft 111 using any suitable technique, such as adhesive bonding, radiofrequency welding, compression fit, overmolding, etc. The cannula hub 112 may be formed from any suitable medical-grade material, such as plastics, metals, etc.

Figure 2:
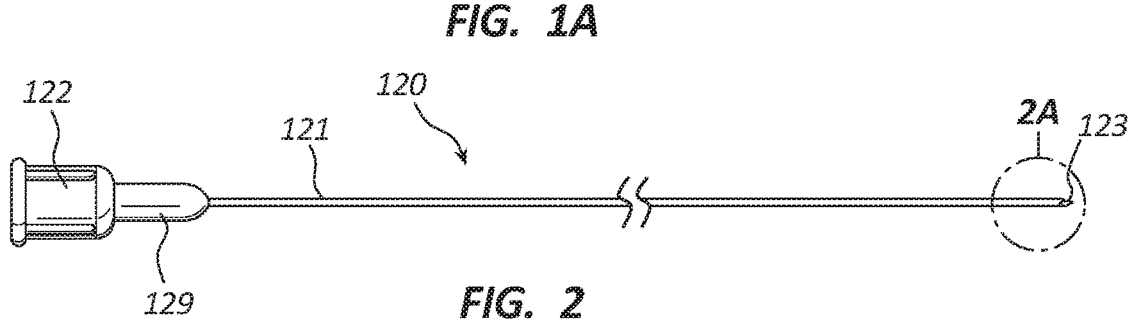
FIG. 2 is a side view of a trocar of a cyst needle assembly.
Figure 2A:
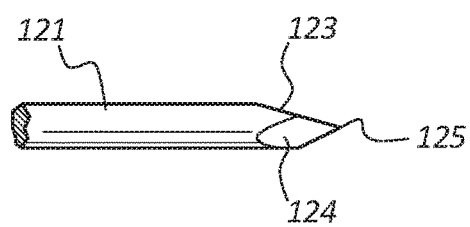
FIG. 2A is a side view of a distal portion of the trocar of FIG. 2.

FIGS. 2-2A illustrate an embodiment of the trocar 120. The trocar 120 is comprised of a trocar shaft 121 and a trocar hub 122. The trocar shaft 121 is a solid cylinder. A trocar distal end 123 is configured to penetrate tissue, such as skin, ligament, membrane, etc. As shown in FIG. 2A, the distal end 123 comprises a plurality of facets 124 and a sharp point 125. The sharp point 125 and the facets 124 are configured to penetrate and cut tissue as the trocar 120 is inserted into the tissue of a patient. The trocar shaft 121 may be formed from stainless steel. In other embodiments, the trocar shaft 121 may be formed from any suitable medical-grade metal material, such as nitinol, titanium, etc. The trocar shaft 121 is configured to be slidingly co-axially disposed within the lumen 114 of the tubular shaft 111.

With continued reference to FIG. 2, the trocar hub 122 is coupled to and disposed at a proximal end of the trocar shaft 121. The trocar hub 122 may be configured to be gripped by fingers of a clinician. In some embodiments, the trocar hub 122 may be generally cylindrical in shape and comprise ribs or other features to enhance gripability. The trocar hub 122 comprises a distally extending portion 129 that is configured to be disposed within the internal cavity 118 of the cannula hub 112. In some embodiments the internal cavity 118 and the extending portion 129 may have matching tapers to enhance coupling of the cannula hub 112 and the trocar hub 122. In other embodiments, the trocar hub 122 and the cannula hub 112 may be releasably coupled using any suitable technique, such as snap fit, threaded connection, bayonet connection, etc. The trocar shaft 121 may be coupled to the extending portion 129 using any suitable technique, such as adhesive bonding, radiofrequency welding, compression fit, overmolding, etc. The trocar hub 122 may be formed from any suitable medical-grade material, such as plastics, metals, etc.

Figure 3:
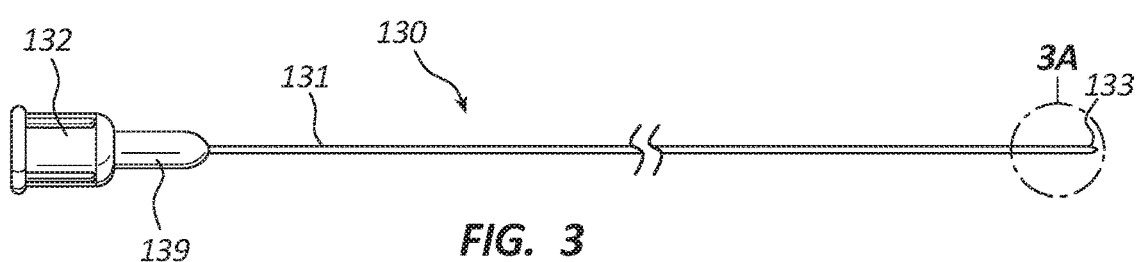
FIG. 3 is a side view of a piercing needle of a cyst needle assembly.
Figure 3A:
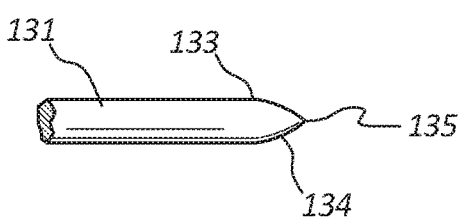
FIG. 3A is a side view of a distal portion of the piercing needle of FIG. 3.

FIGS. 3-3B illustrate an embodiment of the piercing needle 130. The piercing needle 130 is comprised of a flexible shaft 131 and a piercing needle hub 132. The flexible shaft 131 is a solid cylinder. A distal end 133 of the flexible shaft 131 is configured to penetrate tissue, such as skin, ligament, membrane, etc. As shown in FIG. 3A, the distal end 123 is formed in a pencil point shape that includes a radius or taper 134 and a sharp point 135. The sharp point 135 is configured to penetrate tissue, such as ligament and membrane tissues, as the piercing needle 130 is directed to a cyst. In some embodiments, the piercing needle 130 may be formed from nitinol. The piercing needle 130 is configured to be flexible to facilitate passage through a tortuous path, such as a facet joint. The flexible shaft 131 is configured to be slidingly co-axially disposed within the lumen 114 of the tubular shaft 111.

With continued reference to FIG. 3, the piercing needle hub 132 is coupled to and disposed at a proximal end of the flexible shaft 131. The piercing needle hub 132 may be configured to be gripped by fingers of a clinician. In some embodiments, the piercing needle hub 132 may be generally cylindrical in shape and comprise ribs or other features to enhance gripability. The piercing needle hub 132 comprises a distally extending portion 139 that is configured to be disposed within the internal cavity 118 of the cannula hub 112. In some embodiments the internal cavity 118 and the extending portion 139 may have matching tapers to enhance coupling of the cannula hub 112 and the piercing needle hub 132. In other embodiments, the piercing needle hub 132 and the cannula hub 112 may be releasably coupled using any suitable technique, such as snap fit, threaded connection, bayonet connection, etc. The flexible shaft 131 may be coupled to the extending portion 139 using any suitable technique, such as adhesive bonding, radiofrequency welding, compression fit, overmolding, etc. The piercing needle hub 132 may be formed from any suitable medical-grade material, such as plastics, metals, etc.

Figure 4A:
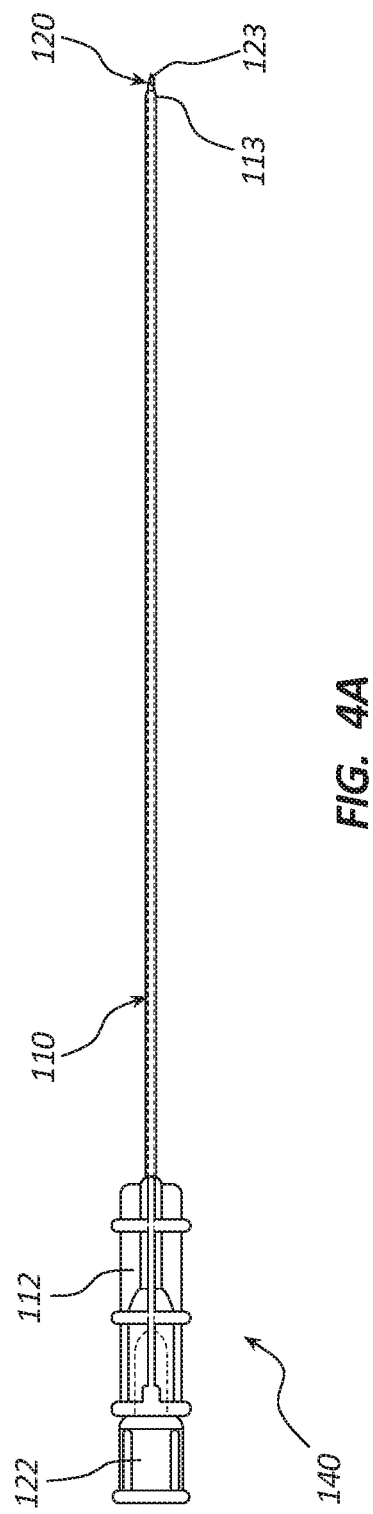
FIG. 4A is a side view of a nested assembly of the introducer cannula of FIG. 1 and the trocar of FIG. 2.

FIG. 4A shows a nested needle assembly 140 comprising the introducer cannula 110 and the trocar 120. The trocar 120 is co-axially disposed within the introducer cannula 110 such that the distal end 123 of the trocar 120 extends beyond the distal end 113 of the introducer cannula 110. The trocar hub 122 is coupled to the cannula hub 112. The distal end 123 of the trocar 120 is configured to penetrate tissue, such as skin, ligament, and membrane, to facilitate positioning of the introducer cannula 110 at a target location within a patient.

Figure 4B:
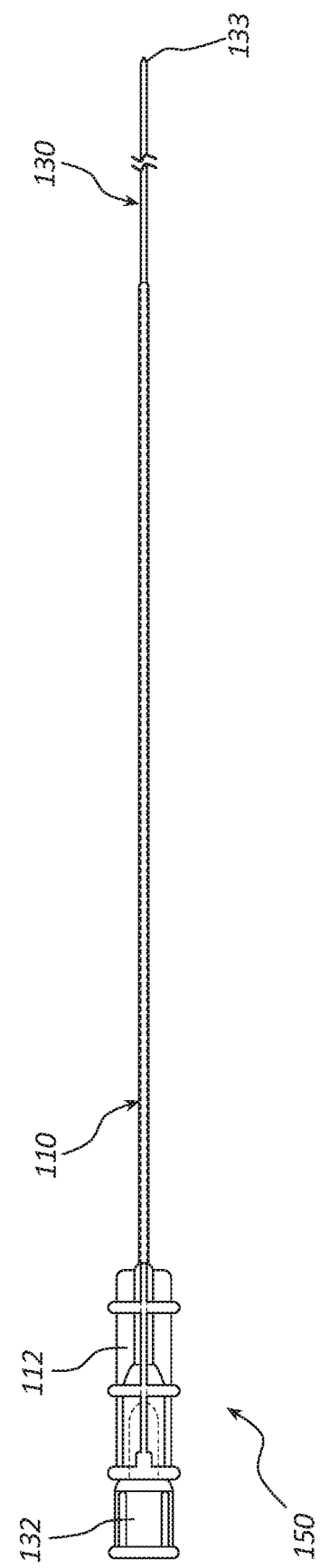
FIG. 4B is a side view of a nested assembly of the introducer cannula of FIG. 1 and the piercing needle of FIG. 3.

FIG. 4B is an illustration of a nested needle assembly 150 of the introducer cannula 110 and the piercing needle 130. The piercing needle 130 is co-axially disposed within the introducer cannula 110. A portion of the piercing needle 130 extends beyond the distal end 113 of the introducer cannula 110. The length of the flexible shaft 131 that extends beyond the introducer cannula 110 may range from about 0.2 cm to about 3 cm, including from about 0.5 cm to about 1 cm, or from about 1.5 cm to about 2.5 cm, or from about 0.2 cm to about 2 cm.

Figure 5:
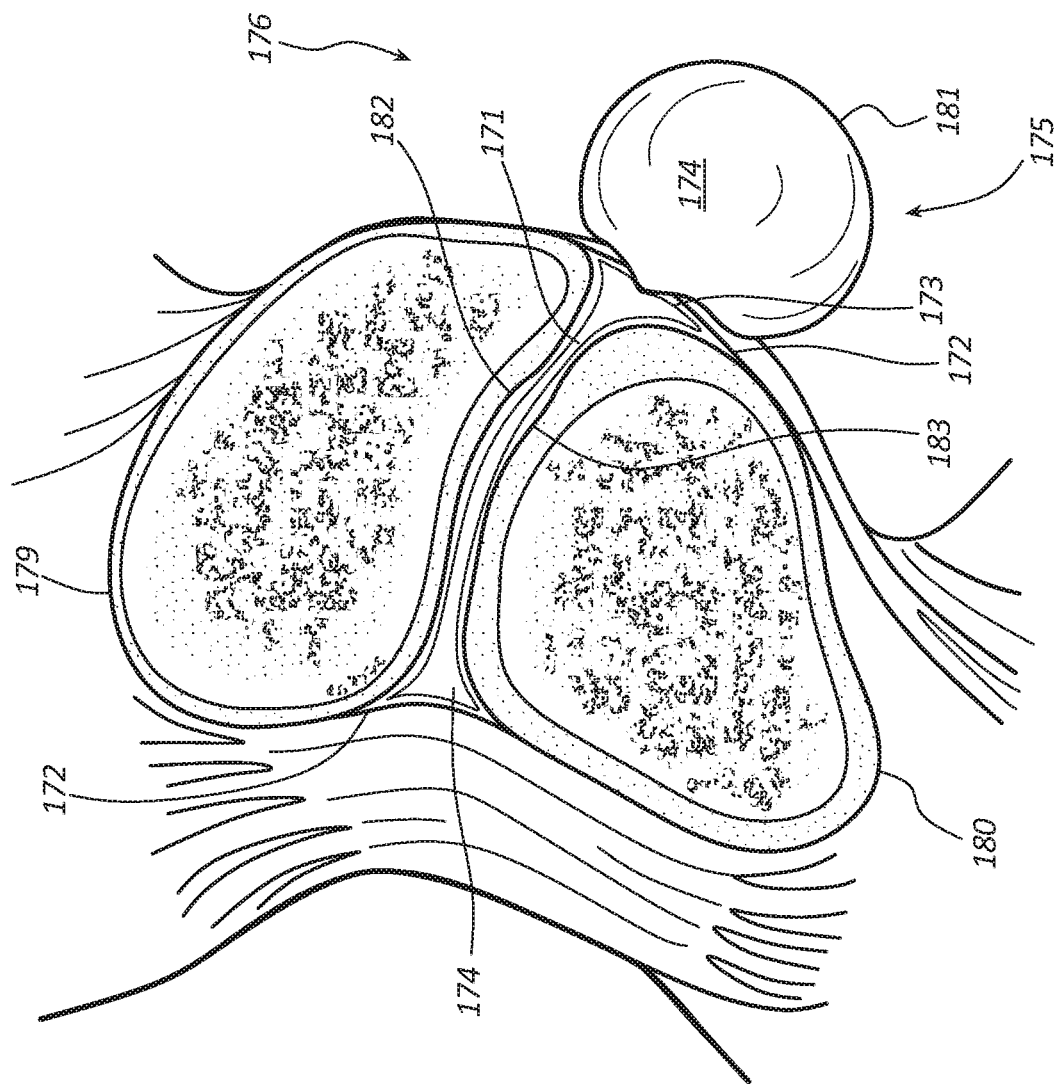
FIG. 5 is a graphical illustration of a portion of a patient's spinal column related to a spinal cyst.

In certain instances the cyst needle assembly 100 may be utilized to access and microfenestrate a spinal cyst, such as a synovial or Tarlov cyst. The cyst may be disposed within the spinal column such that portions of the vertebrae impede access to the cyst with a spinal needle to drain the cyst. FIG. 5 is an exemplary graphical illustration of the spinal anatomy associated with a spinal synovial cyst 175. The cyst 175 is disposed within a spinal column 176. The cyst 175 is a sack filled with synovial fluid 174 and surrounded by a synovium 181. The cyst 175 may be in fluid communication with a facet joint 171. The facet joint 171 comprises a cavity filled with synovial fluid 174. A synovial membrane 173 surrounds the cavity. The facet joint 171 is formed between a superior facet 179 and an inferior facet 180 of the vertebrae. A superior facet joint surface 182 is concavely curved while an inferior facet joint surface 183 is convexly curved. The superior facet 179 and the inferior facet 180 are coupled together by capsular ligaments 172.

Figure 6A:
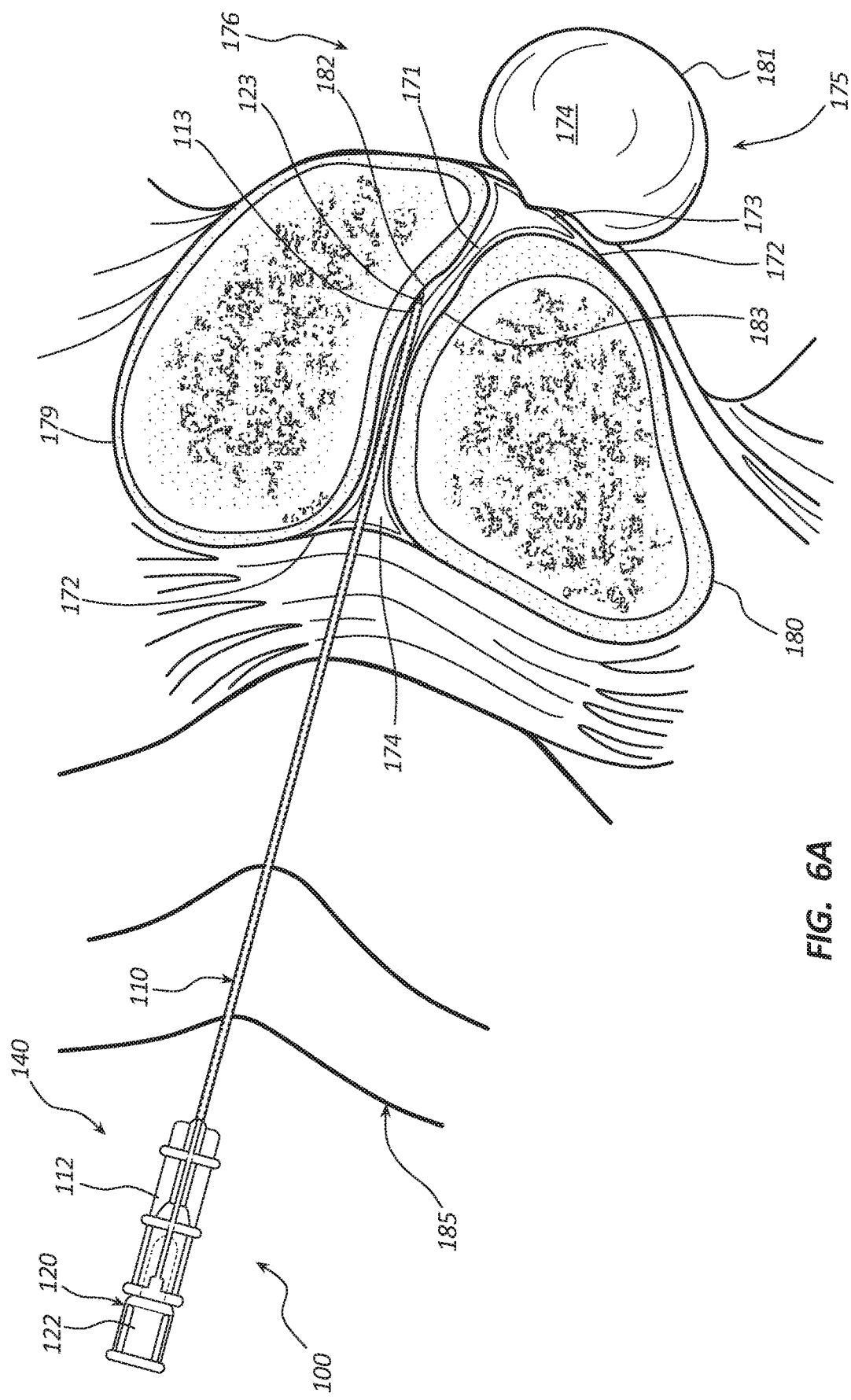
FIG. 6A is a side view of the nested assembly of FIG. 4A disposed within a facet joint of FIG. 5.
Figure 6B:
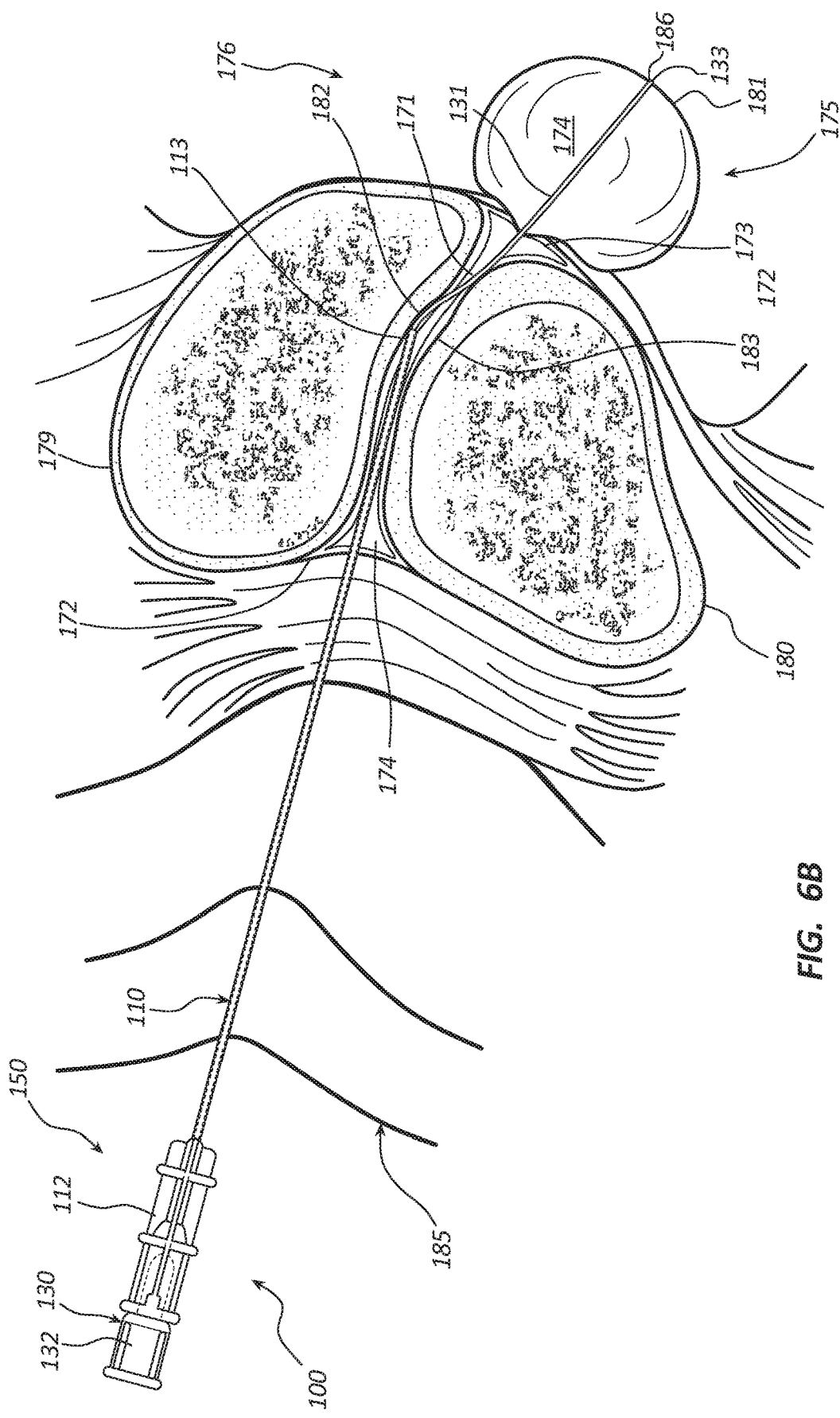
FIG. 6B is a side view of the nested needle assembly of FIG. 4B disposed within the facet joint of FIG. 5 and the piercing needle of FIG. 3 fenestrating the cyst of FIG. 5.

In use, referring to FIGS. 6A-6B, the nested needle assembly 140 of FIG. 4A, comprising the introducer cannula 110 and the trocar 120, is percutaneously inserted through skin 185 of a patient and into the facet joint 171, such as under computed tomography guidance. The sharpened distal end 123 facilitates penetration of the trocar 120 and the introducer cannula 110 through the skin 185, the capsular ligament 172, the synovial membrane 173, and other tissues. The distal end 113 of the introducer cannula 110 is positioned as far into the facet joint 171 as possible as shown in FIG. 6A. A curvature of the facet joint 171 created by the concave curvature of the superior facet joint surface 182 and the convex curvature of the inferior facet joint surface 183 may prevent the nested needle assembly 140 from passing entirely through the facet joint 171. The trocar 120 may be displaced proximally with respect to the introducer cannula 110 to remove the trocar 120 from the introducer cannula 110.

As illustrated in FIG. 6B, the piercing needle 130 may then be inserted into the introducer cannula 110 to form the nested needle assembly 150 of FIG. 4B. Due to the flexibility of the flexible shaft 131, the piercing needle 130 may navigate the curvature of the facet joint 171 as the piercing needle 130 is displaced distally. The distal end 123 of the piercing needle 130 may pierce the synovial membrane 173 and the capsular ligament 172 prior to accessing the cyst 175 and forming an opening, such as a microfenestration 186 in the synovium 181. The microfenestration 186 may allow drainage of the synovial fluid 174 from the cyst 175 resulting in decompression of the spinal column 176 and/or root nerve.

FIGS. 7-11C depict an embodiment of a cyst needle assembly 200 that resembles the cyst needle assembly 100 described above in certain respects. Accordingly, like features are designated with like reference numerals, with the leading digit incremented to "2." For example, the embodiment depicted in FIG. 7 includes an introducer needle 210 that may, in some respects, resemble the introducer cannula 110 of FIG. 1. Relevant disclosure set forth above regarding similarly identified features thus may not be repeated hereafter. Moreover, specific features of the cyst needle assembly 100 and related components shown in FIGS. 1-6B may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply analogously to the features of the cyst needle assembly 200 and related components depicted in FIGS. 7-11C. Any suitable combination of the features, and variations of the same, described with respect to the cyst needle assembly 100 and related components illustrated in FIGS. 1-6B can be employed with the cyst needle assembly 200 and related components of FIGS. 7-11C, and vice versa.

FIGS. 7-11C depict an embodiment of the cyst needle assembly 200. In the illustrated embodiment, the cyst needle assembly 200 is comprised of a first elongate member, introducer cannula 210; a second elongate member, inner cannula 220; and a piercing needle 230.

Figure 7:
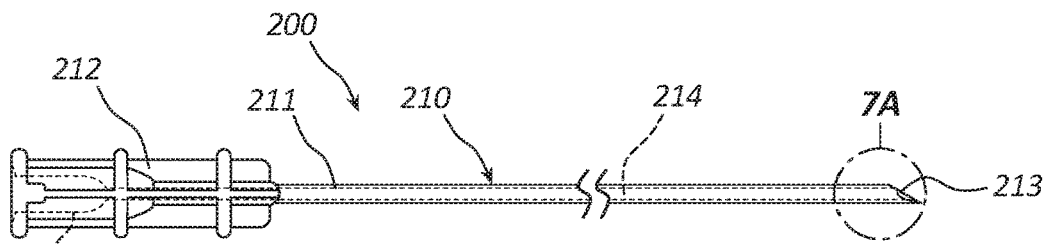
FIG. 7 is a side view of an introducer cannula of a cyst needle assembly.
Figure 7A:
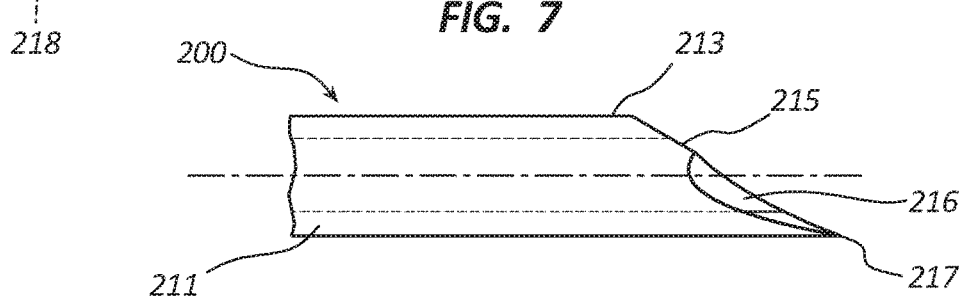
FIG. 7A is a side view of a distal portion of the introducer cannula of FIG. 7.

As illustrated in FIGS. 7-7A, the introducer cannula 210 comprises a tubular shaft 211 and a cannula hub 212. The tubular shaft 211 has a lumen 214 and a distal end 213. The distal end 213 is sharpened and configured to penetrate tissue. In other words, the distal end 213 can be pushed against tissue, such as skin, and will puncture or cut the tissue. As illustrated in FIG. 7A, the distal end 213 may comprise a bevel 215 that is angled relative to the longitudinal axis of the tubular shaft 211. In the illustrated embodiment, the bevel 215 comprises one or more lancets 216 disposed on a lateral edge of the bevel 215. The lancets 216 are configured to cut tissue as the introducer cannula 210 is inserted into tissue. The bevel 215 also comprises a sharp point 217 that is configured to penetrate tissue. In other embodiments, the distal end 213 may be shaped in any suitable shape, such as a Quinke bevel, a Pitkin bevel, a Greene bevel, a Tuohy bevel, etc. In some embodiments, the tubular shaft 211 may be formed from any suitable medical-grade metal, such as stainless steel, titanium, nitinol, etc. The outer diameter of the tubular shaft 211 may range from 18 gauge to 25 gauge, including from 20 gauge to 22 gauge. The length of the tubular shaft 111 may range from about 2.5 cm to about 23 cm, including from about 8 cm to about 18 cm, or from about 4 cm to about 6 cm, or from 5 cm to 23 cm, or from about 2.5 cm to about 8 cm.

With continued reference to FIG. 7, the cannula hub 212 is coupled to and disposed at a proximal end of the tubular shaft 211. The cannula hub 212 may be configured to be gripped by fingers of a clinician. In some embodiments, the cannula hub 212 may be generally cylindrical in shape and comprise ribs or other features to enhance gripability. The cannula hub 212 comprises an internal cavity 218 that is in fluid communication with the lumen 214 of the tubular shaft 211. The internal cavity 218 may be configured to receive a portion of the inner cannula 220 (not shown) as will be further described below. The cannula hub 212 may be coupled to the tubular shaft 211 using any suitable technique, such as adhesive bonding, radiofrequency welding, compression fit, overmolding, etc. The cannula hub 212 may be formed from any suitable medical-grade material, such as plastics, metals, etc.

Figure 8:
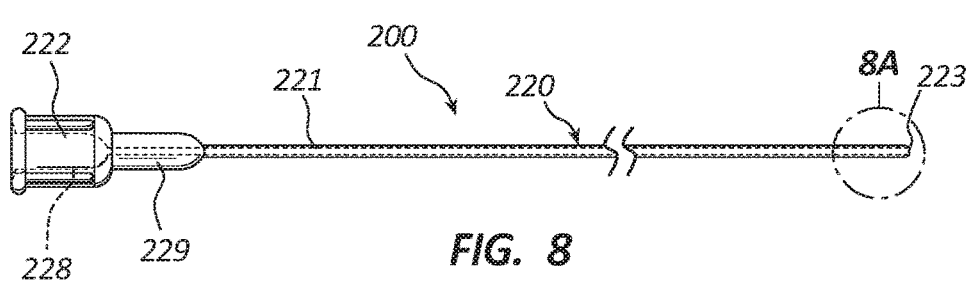
FIG. 8 is a side view of an inner cannula of a cyst needle assembly.
Figure 8A:
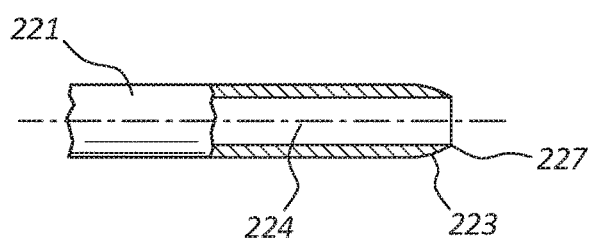
FIG. 8A is a side view of a distal portion of the inner cannula of FIG. 8.

FIGS. 8-8A illustrate an embodiment of the inner cannula 220 of the cyst needle assembly 200. The inner cannula 220 is comprised of a tubular shaft 221 and an inner cannula hub 222. A distal end 223 of the inner cannula 220 is configured to resist penetrating tissue. As illustrated in FIG. 8A, the distal end 223 is radiused to form a blunt tip 227 such that the inner cannula 220 will resist penetrating tissue when the distal end 223 is pushed against tissue, such as skin or membranes. The inner cannula shaft 221 may be configured to be flexible such that the inner cannula shaft 221 can be navigated through a tortuous path. For example, the flexibility of the inner cannula shaft 221 may facilitate passage of the inner cannula shaft 221 through a facet joint of the spine as will be described below. The inner cannula shaft 221 may be formed from any suitable medical-grade metal material, such as nitinol, titanium, stainless steel, etc. The inner cannula shaft 221 is configured to be slidingly co-axially disposed within the lumen 214 of the cannula shaft 211.

With continued reference to FIG. 8, the inner cannula hub 222 is coupled to and disposed at a proximal end of the inner cannula shaft 221. The inner cannula hub 222 may be configured to be gripped by fingers of a clinician. In some embodiments, the inner cannula hub 222 may be generally cylindrical in shape and comprise ribs or other features to enhance gripability. The inner cannula hub 222 comprises a distally extending portion 229 that is configured to be disposed within the internal cavity 218 of the cannula hub 212 such that the inner cannula hub 222 and the cannula hub 212 may be releasably coupled. In some embodiments the internal cavity 218 and the extending portion 229 may have matching tapers to enhance coupling of the cannula hub 212 and the inner cannula hub 222. In other embodiments, the inner cannula hub 222 and the cannula hub 212 may be releasably coupled using any suitable technique, such as snap fit, threaded connection, bayonet connection, etc. The inner cannula hub 222 comprises an internal cavity 228 that is in fluid communication with a lumen 224 of the inner cannula shaft 221. The internal cavity 228 may be configured to receive a portion of a piercing needle hub 232 (not shown) as will be described below. The inner cannula shaft 221 may be coupled to the extending portion 229 using any suitable technique, such as adhesive bonding, radiofrequency welding, compression fit, overmolding, etc. The inner cannula hub 222 may be formed from any suitable medical-grade material, such as plastics, metals, etc.

Figure 9:
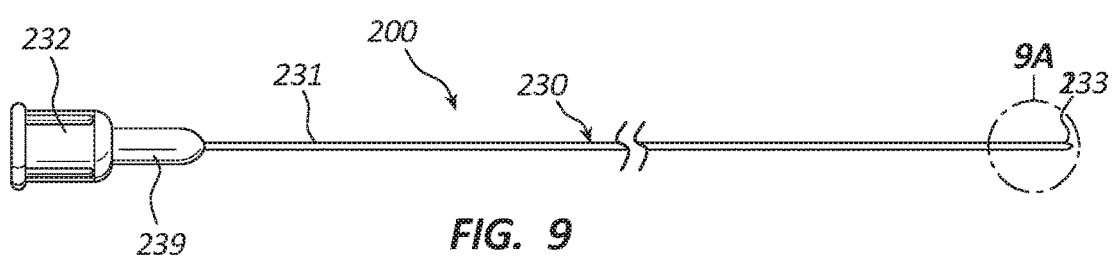
FIG. 9 is a side view of a piercing needle of a cyst needle assembly.
Figure 9A:
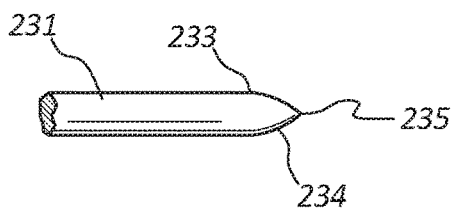
FIG. 9A is a side view of a distal portion of the piercing needle of FIG. 9.

FIGS. 9-9A illustrate an embodiment of the piercing needle 230 of the cyst needle assembly 200. The piercing needle 230 is comprised of a flexible shaft 231 and a piercing needle hub 232. The flexible shaft 231 may be a solid cylinder. A distal end 233 of the flexible shaft 231 is configured to penetrate tissue, such as skin, ligament, membrane, etc. As shown in FIG. 9A, the distal end 233 is formed in a pencil point shape that includes a radius or taper 234 and a sharp point 235. The sharp point 235 is configured to penetrate tissue, such as ligament and membrane tissues, as the piercing needle 230 is directed to a cyst or other body lesion. The piercing needle 230 may be formed from nitinol or any other suitable material. The piercing needle 230 is configured to be flexible to facilitate passage through a tortuous path, such as a facet joint. The flexible shaft 231 is configured to be slidingly co-axially disposed within the lumen 214 of the cannula shaft 211.

With continued reference to FIG. 9, the piercing needle hub 232 is coupled to and disposed at a proximal end of the flexible shaft 231. The piercing needle hub 232 may be configured to be gripped by fingers of a clinician. In some embodiments, the piercing needle hub 232 may be generally cylindrical in shape and comprise ribs or other suitable feature to enhance gripability. The piercing needle hub 232 comprises a distally extending portion 239 that is configured to be disposed within the internal cavity 228 of the inner cannula hub 222. In some embodiments the internal cavity 228 and the extending portion 239 may have matching tapers to enhance coupling of the inner cannula hub 222 and the piercing needle hub 232. In other embodiments, the inner cannula hub 222 and the piercing needle hub 232 may be releasably coupled using any suitable technique, such as snap fit, threaded connection, bayonet connection, etc. The flexible shaft 231 may be coupled to the extending portion 239 using any suitable technique, such as adhesive bonding, radiofrequency welding, compression fit, overmolding, etc. The piercing needle hub 232 may be formed from any suitable medical-grade material, such as plastics, metals, etc.

Figure 10:
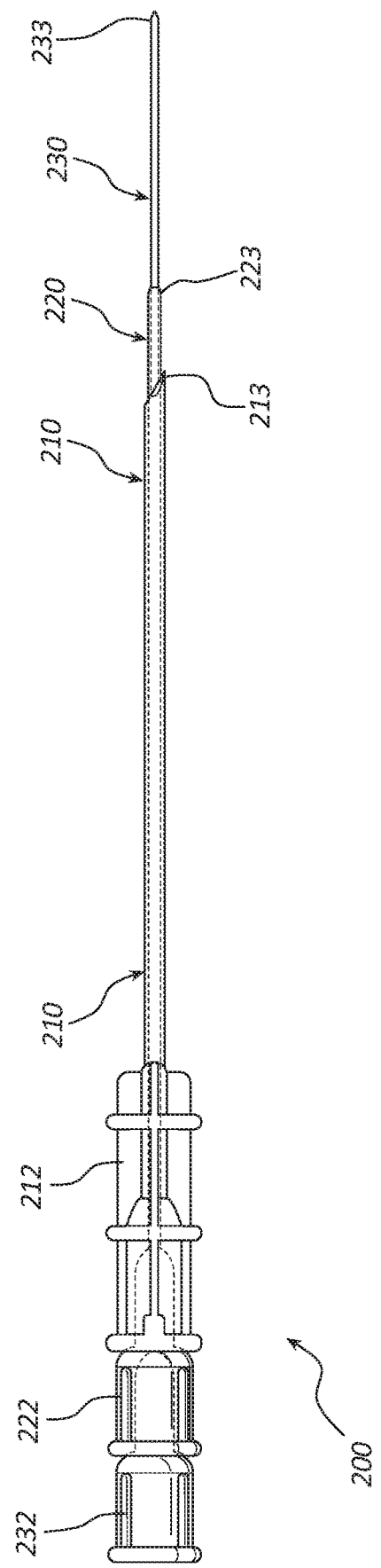
FIG. 10 is a side view of a nested needle assembly of the introducer cannula of FIG. 7, the inner cannula of FIG. 8, and the piercing needle of FIG. 9.

FIG. 10 shows the cyst needle assembly 200. The inner cannula 220 is co-axially disposed within the introducer cannula 210 such that the distal end 223 of the inner cannula 220 extends beyond the distal end 213 of the introducer cannula 210 and the cannula hub 212 is coupled to the inner cannula hub 222. In other embodiments, the inner cannula 220 may not extend beyond the distal end 213. The length of the inner cannula 220 that extends beyond the introducer cannula 210 may range from an about 0.0 cm to about 3 cm, including about 1 cm to about 2 cm, or from about 0.5 cm to about 3 cm. The piercing needle 230 is co-axially disposed within the inner cannula 220. A portion of the piercing needle 230 extends beyond the distal end 223 of the inner cannula 220. In other embodiments the piercing needle 230 may not extend beyond the distal end 223. The length of the piercing needle 230 that extends beyond the inner cannula 220 may range from about 0.0 cm to about 3.5 cm, including from about 0.5 cm to about 1.5 cm, or from about 0.25 cm to about 3.5 cm.

Figure 11A:
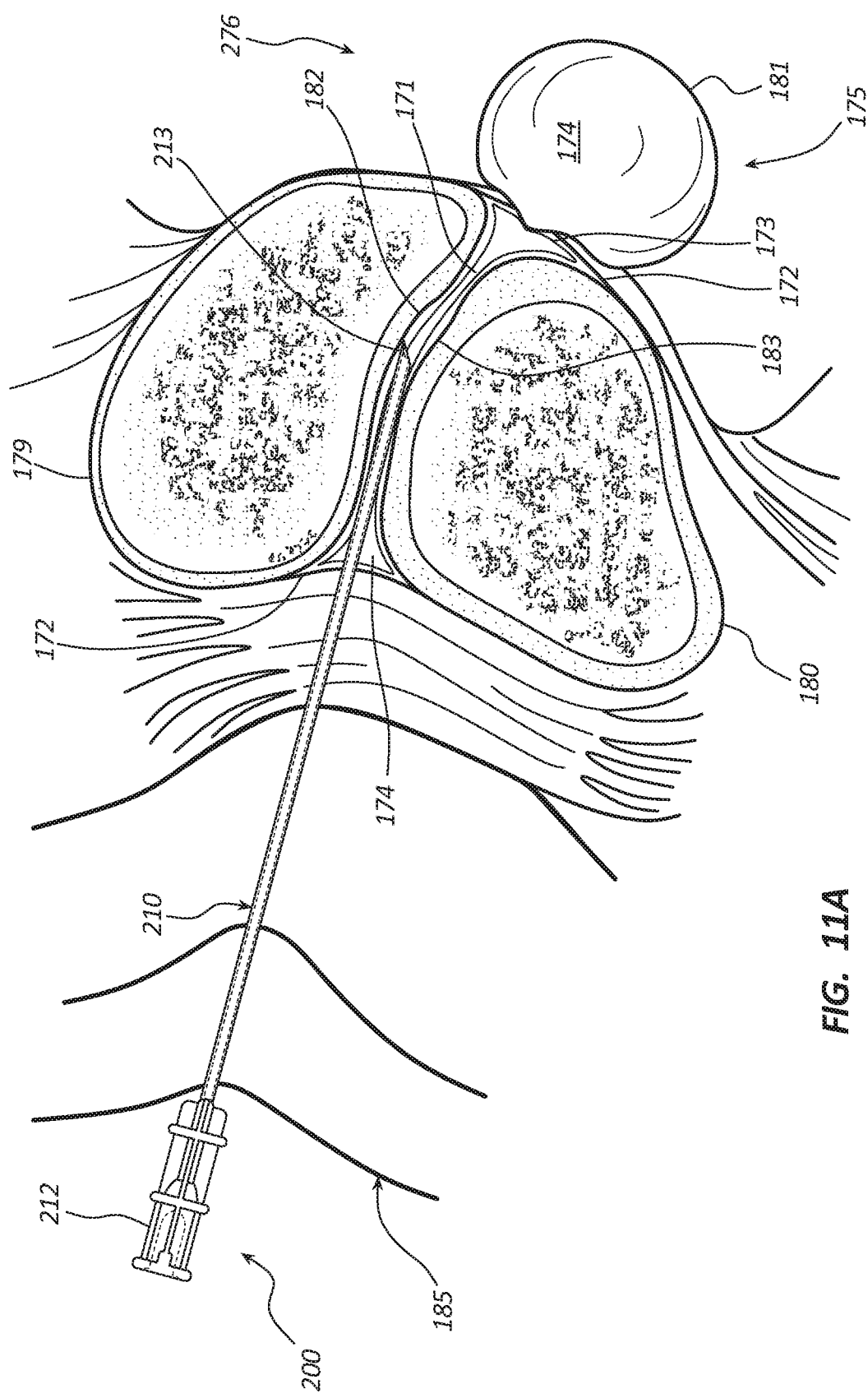
FIG. 11A is a side view of the introducer cannula of FIG. 7 disposed within the facet joint of FIG. 5.

In certain instances the cyst needle assembly 200 may be utilized to access and create an opening in a spinal cyst, such as a synovial or Tralov cyst. The cyst may be disposed within the spinal column 176 as illustrated in FIG. 5. In use, referring to FIGS. 11A-11C, the introducer cannula 210 is percutaneously inserted through the skin 185 of a patient and into the facet joint 171, such as under computed tomography guidance. The sharpened distal end 213 facilitates penetration of the introducer cannula 210 through the skin, the capsular ligament 172, the synovial membrane 173, and other tissues. The distal end 213 of the introducer cannula 210 is positioned as deep into the facet joint 171 as possible, as shown in FIG. 11A. A curvature of the facet joint 171 created by the concave curvature of the superior facet joint surface 182 and the convex curvature of the inferior facet joint surface 183 may prevent the introducer cannula 210 from passing entirely through the facet joint 171.

Figure 11B:
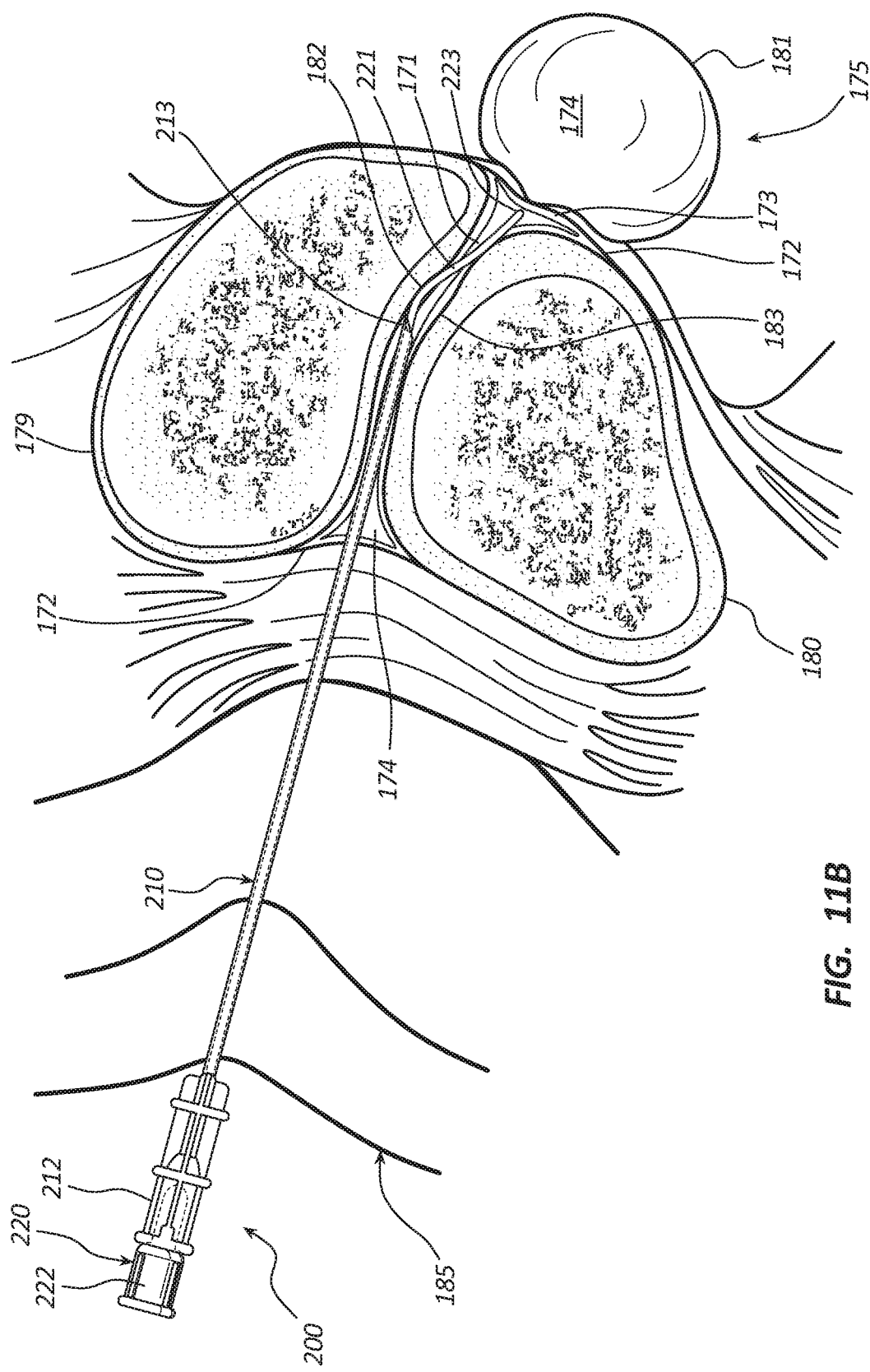
FIG. 11B is a side view of a nested assembly of the introducer cannula of FIG. 7 and the inner cannula of FIG. 8 disposed within the facet joint of FIG. 5.

As illustrated in FIG. 11B, the inner cannula 220 is coaxially inserted through the introducer cannula 210 and into the facet joint 171. The inner cannula 220 is advanced as far as possible into the facet joint 171 or until the distal end 223 is disposed adjacent the synovial membrane 173. In some instances, the distal end 223 may not extend into the facet joint 171 or may extend into the facet joint 171 a short distance due to the curvature of the facet joint 171. The bluntness of the distal end 223 is configured to allow flexible passage through the facet joint and to prevent penetration of the inner cannula 220 through the synovial membrane 173. In other embodiments, the inner cannula 220 may be configured to penetrate the synovial membrane 173. The inner cannula 220 may be advanced into the facet joint 171 until the inner cannula hub 222 is coupled with the cannula hub 212 or until resistance to advancement of the inner cannula 220 is felt by the clinician.

Figure 11C:
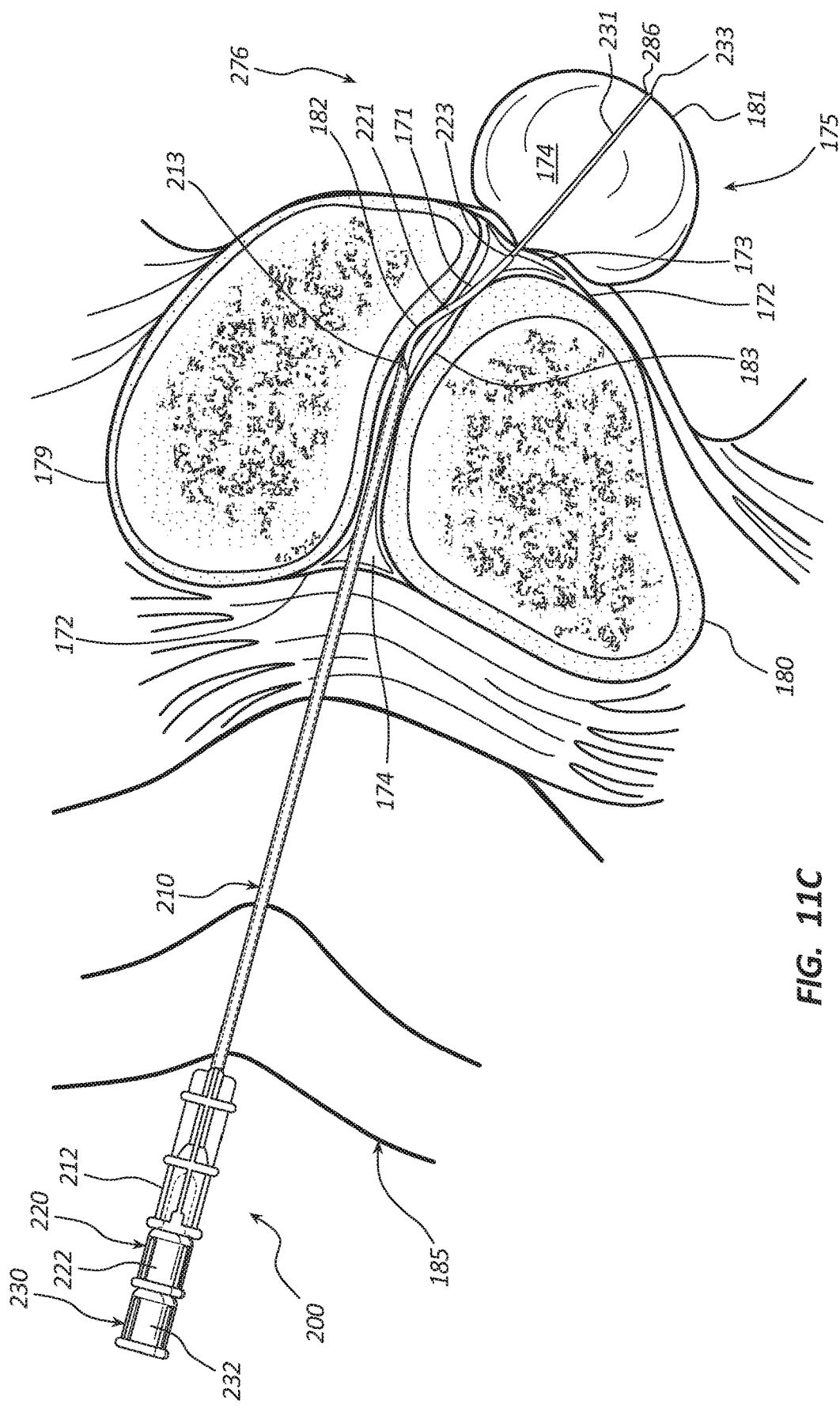
FIG. 11C is a side view of a nested assembly of the introducer cannula of FIG. 7, the inner cannula of FIG. 8, and the piercing needle of FIG. 9 disposed within the facet joint of FIG. 5 and the piercing needle fenestrating the cyst of FIG. 5.

As illustrated in FIG. 11C, the piercing needle 230 is coaxially inserted through the inner cannula hub 222, through the inner cannula shaft 221, and into the facet joint 171. The distal end 233 of the piercing needle 230 extends beyond the distal end 223 of the inner cannula 220 and may pierce the synovial membrane 173 and the capsular ligament 172 prior to accessing and piercing the synovium 181 of the cyst 175, to create an opening such as microfenestration 186. The microfenestration 186 may allow drainage of the synovial fluid 174 from the cyst 175 resulting in decompression of the spinal column 176 and/or root nerve.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

References to approximations are made throughout this specification, such as by use of the term "substantially." For each such reference, it is to be understood that, in some embodiments, the value, feature, or characteristic may be specified without approximation. For example, where qualifiers such as "about" and "substantially" are used, these terms include within their scope the qualified words in the absence of their qualifiers. For example, where the term "substantially perpendicular" is recited with respect to a feature, it is understood that in further embodiments, the feature can have a precisely perpendicular configuration.

Similarly, in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment.

The claims following this written disclosure are hereby expressly incorporated into the present written disclosure, with each claim standing on its own as a separate embodiment. This disclosure includes all permutations of the independent claims with their dependent claims. Moreover, additional embodiments capable of derivation from the independent and dependent claims that follow are also expressly incorporated into the present written description.

Without further elaboration, it is believed that one skilled in the art can use the preceding description to utilize the invention to its fullest extent. The claims and embodiments disclosed herein are to be construed as merely illustrative and exemplary, and not a limitation of the scope of the present disclosure in any way. It will be apparent to those having ordinary skill in the art, with the aid of the present disclosure, that changes may be made to the details of the above-described embodiments without departing from the underlying principles of the disclosure herein. In other words, various modifications and improvements of the embodiments specifically disclosed in the description above are within the scope of the appended claims. Moreover, the order of the steps or actions of the methods disclosed herein may be changed by those skilled in the art without departing from the scope of the present disclosure. In other words, unless a specific order of steps or actions is required for proper operation of the embodiment, the order or use of specific steps or actions may be modified. The scope of the invention is therefore defined by the following claims and their equivalents.

The invention claimed is:

1. A percutaneous needle assembly for synovial cyst access, comprising:
   a first rigid elongate member comprising a lumen;
   a second rigid elongate member coaxially disposed within the lumen of the first elongate member; and
   a piercing needle,
   wherein one of the first elongate member and the second elongate member comprises a sharp distal end configured to penetrate tissue and the other of the first elongate member and the second elongate member comprises a blunt distal end,
   wherein both the first elongate member and the second elongate member are straight,
   wherein the piercing needle comprises a shaft and a sharp distal point configured to pass through a tortuous path and penetrate a tissue, and
   wherein the shaft and the sharp distal point are fabricated from a flexible material.

2. The percutaneous needle assembly of claim 1, wherein the first elongate member comprises the blunt distal end, wherein the blunt distal end is configured to resist penetrating tissue.

3. The percutaneous needle assembly of claim 1, wherein the first elongate member comprises the sharp distal end, and wherein the sharp distal end is beveled.

4. The percutaneous needle assembly of claim 1, wherein the second elongate member comprises the blunt distal end and a lumen extending from the blunt distal end to a proximal end, and wherein the blunt distal end is configured to resist penetrating tissue.

5. The percutaneous needle assembly of claim 4, wherein the piercing needle is coaxially disposed within the lumen of the second elongate member and extends beyond the distal end of the second elongate member.

6. The percutaneous needle assembly of claim 1, wherein the second elongate member comprises the sharp distal end.

7. The percutaneous needle assembly of claim 1, wherein the piercing needle is coaxially disposed within the lumen of the first elongate member and extends beyond a distal end of the first elongate member.

8. The percutaneous needle assembly of claim 1, wherein the piercing needle comprises a distal end configured to penetrate tissue.

9. The percutaneous needle assembly of claim 1, wherein the piercing needle is formed from nitinol.

10. A kit for creating an opening in a wall of a spinal cyst, comprising:
    a spinal cyst needle assembly, comprising:
        a first rigid needle;
        a second rigid needle configured to be coaxially disposed within the first needle; and
        a piercing needle,
    wherein one of the first needle and the second needle comprises a sharp distal end configured to penetrate tissue and the other of the first needle and the second needle comprises a blunt distal end,
    wherein both the first needle and the second needle are straight, wherein the piercing needle comprises a shaft and a sharp distal point configured to pass through a tortuous path and penetrate a tissue, and wherein the shaft and the sharp distal point are fabricated from a flexible material.

11. The kit of claim 10, wherein the first needle comprises the blunt distal end, and wherein the blunt distal end is configured to be tissue non-penetrating.

12. The kit of claim 10, wherein the first needle comprises the sharp distal end.

13. The kit of claim 10, wherein the second needle comprises the blunt distal end, and wherein the blunt distal end is configured to resist penetrating tissue.

14. The kit of claim 10, wherein the piercing needle comprises a sharp distal end configured to penetrate tissue.

15. The kit of claim 10, wherein the piercing needle is configured to create a microfenestration in the wall of a spinal cyst.

\* \* \* \* \*